United States Patent
Gutierrez et al.

(10) Patent No.: US 11,679,993 B2
(45) Date of Patent: Jun. 20, 2023

(54) METHODS, APPARATUS, AND SYSTEMS FOR DETECTING AND REMOVING MICROPLASTICS FROM WATER

(71) Applicant: Aizaco Limited Company, Frisco, TX (US)

(72) Inventors: Carlos Alberto Hernandez Gutierrez, Frisco, TX (US); Aiza Fernanda Jose Sanchez, Frisco, TX (US)

(73) Assignee: AIZACO LIMITED COMPANY, Frisco, TX (US)

(*) Notice: Subject to any disclaimer, the term of this patent is extended or adjusted under 35 U.S.C. 154(b) by 0 days.

(21) Appl. No.: 17/701,499

(22) Filed: Mar. 22, 2022

(65) Prior Publication Data

US 2022/0306488 A1    Sep. 29, 2022

Related U.S. Application Data

(60) Provisional application No. 63/164,609, filed on Mar. 23, 2021.

(51) Int. Cl.
*C02F 1/00* (2023.01)
*B01D 21/00* (2006.01)
(Continued)

(52) U.S. Cl.
CPC .......... *C02F 1/008* (2013.01); *B01D 21/0042* (2013.01); *B01D 29/56* (2013.01);
(Continued)

(58) Field of Classification Search
None
See application file for complete search history.

(56) References Cited

U.S. PATENT DOCUMENTS

| 5,299,141 A | 3/1994 | Hungerford et al. |
| 2010/0170537 A1* | 7/2010 | Gingras ................. B08B 3/022 417/393 |

(Continued)

FOREIGN PATENT DOCUMENTS

| CN | 107670391 A | 2/2018 |
| CN | 110092492 A | 8/2019 |

(Continued)

OTHER PUBLICATIONS

Annex to Partial International Search of PCT/US2022/021423, dated Jun. 22, 2022 by the European Patent Office Acting as Searching Authority.

(Continued)

*Primary Examiner* — Richard C Gurtowski
(74) *Attorney, Agent, or Firm* — Marcella M. Bodner; Cole Schotz, P.C.

(57) ABSTRACT

Methods, apparatus, and systems are provided for detecting and removing microplastics from wastewater effluent. Both, automatic/remote and manual monitoring and sampling components are included to detect the presence of microplastics. The automatic monitoring and sampling component includes a TSS sensor and associated apparatus calibrated to account for non-plastic solids present in the wastewater and, thereby, more accurately determine the presence of microplastics. Efficient separation and removal of microplastics from wastewater effluent is performed by a specialized capture net apparatus having multiple sized mesh components and optional diffuser devices which perform size exclusion filtration of microplastics from the water. In an exemplary embodiment, the methods generally include diverting treated wastewater effluent from a wastewater treatment facility's main line into a wastewater sampling mechanism via an intake pipe, and then into a solids (Continued)

monitoring and separation mechanism which includes the specialized capture net apparatus.

14 Claims, 6 Drawing Sheets

(51) Int. Cl.
| | |
|---|---|
| *B01D 29/56* | (2006.01) |
| *G01N 1/20* | (2006.01) |
| *G01N 15/06* | (2006.01) |
| *G01N 33/18* | (2006.01) |
| *G01N 35/10* | (2006.01) |
| *C02F 101/30* | (2006.01) |

(52) U.S. Cl.
CPC ............... *C02F 1/001* (2013.01); *G01N 1/20* (2013.01); *G01N 15/06* (2013.01); *G01N 33/18* (2013.01); *G01N 35/10* (2013.01); *C02F 2001/007* (2013.01); *C02F 2101/30* (2013.01); *C02F 2209/001* (2013.01); *C02F 2209/10* (2013.01); *C02F 2301/046* (2013.01); *G01N 2015/0693* (2013.01)

(56) References Cited

U.S. PATENT DOCUMENTS

| | | | |
|---|---|---|---|
| 2013/0068679 A1* | 3/2013 | Hannemann | B01D 21/2483 210/170.03 |
| 2015/0191382 A1* | 7/2015 | Blanc | C02F 3/085 210/219 |
| 2020/0115868 A1 | 4/2020 | Curet et al. | |

FOREIGN PATENT DOCUMENTS

| | | |
|---|---|---|
| CN | 111879566 A | 11/2020 |
| WO | 2022204206 | 9/2022 |

OTHER PUBLICATIONS

Invitation to Pay Additional Fees and where applicable protest fees in Partial International Search of PCT/US2022/021423, dated Jun. 22, 2022 by the European Patent Office Acting as Searching Authority.

International Search Report for International Patent Application No. PCT/US2022/021423, dated Sep. 21, 2022.

Written Opinion of the International Searcing Authority for International Patent Application No. PCT/US2022/021423, dated Sep. 21, 2022.

* cited by examiner

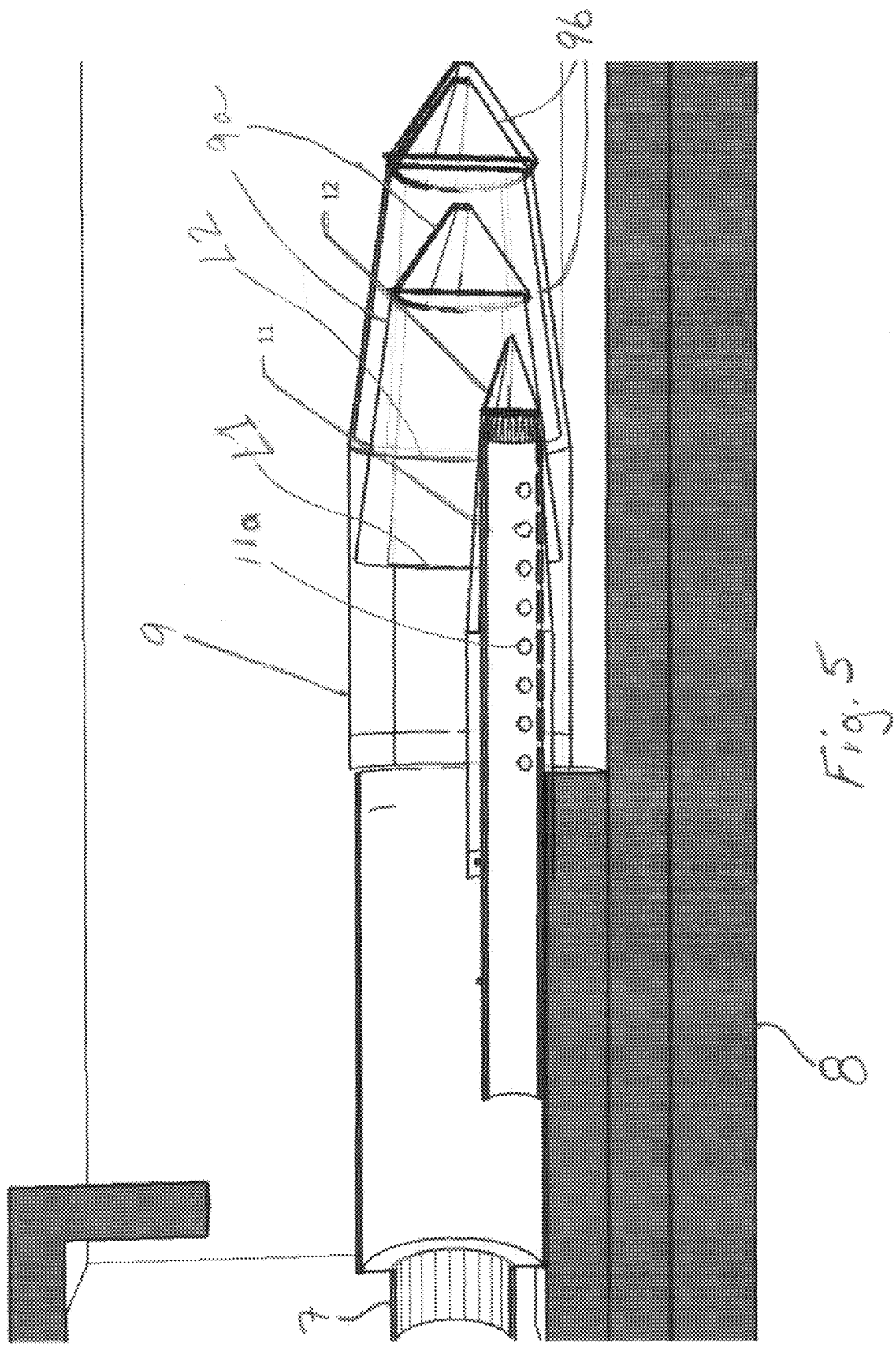

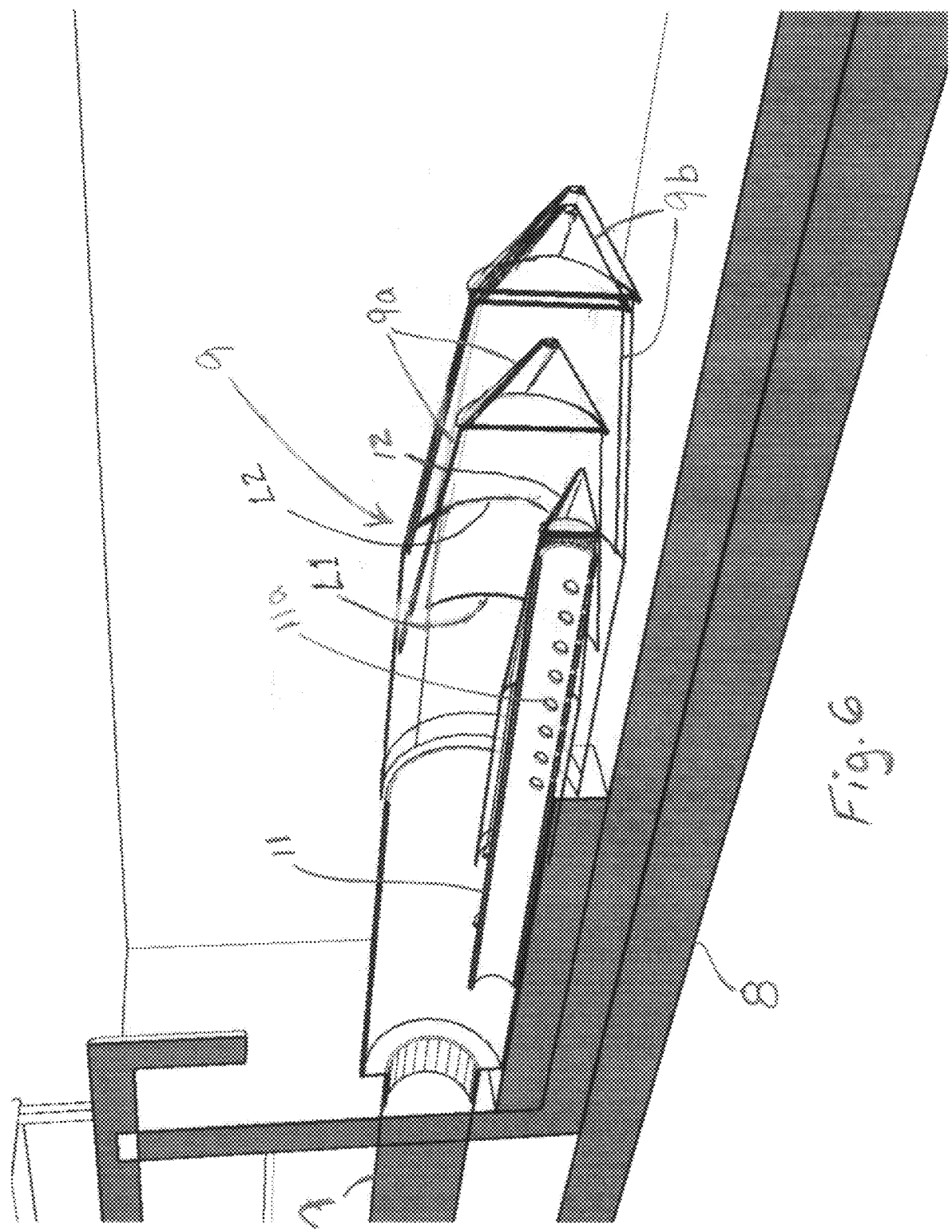

METHODS, APPARATUS, AND SYSTEMS FOR DETECTING AND REMOVING MICROPLASTICS FROM WATER

CROSS-REFERENCE TO RELATED APPLICATIONS

The present application claims the benefit of U.S. Provisional Application No. 63/164,609 filed on Mar. 23, 2021, the entire disclosure of which is hereby incorporated by reference herein.

TECHNICAL FIELD

The present invention relates to the detection and removal of microplastics from water streams, such as wastewater effluent streams. More particularly, the present invention relates to continuous automatic and remote monitoring, sampling, detection, separation and removal of microplastics from treated wastewater effluent.

BACKGROUND

The growth in first world economies and the urbanization of developing countries continues to strain global water supplies. While technology utilized at water treatment facilities, including wastewater treatment plants, continues to advance, such facilities remain overburdened and often fall short when it comes to treating water to the point that it may be reused for agricultural and human consumption. Unfortunately, pollution today is more than just bulk items such as water bottles and trash, and today's wastewater treatment plants are not designed to handle some new forms of pollutants.

In particular, wastewater treatment plants and their technologies are now facing difficulties when it comes to separation and removal of smaller impurities, such as microplastics, many of which cause adverse impacts upon the environment. Such newer smaller impurities include microplastics which are generally defined as plastic particles having sizes smaller than about 5 millimeters. It might be said that wastewater treatment plants, together with non-point sources (e.g., stormwater discharges), are now among the primary sources of microplastics in fresh waters and the ocean because microplastics escape removal by conventional wastewater treatment technologies, whereupon they enter surface freshwaters and oceans and contaminate water resources like groundwater which might otherwise be reusable, and negatively impact terrestrial and aquatic environments.

Thus, there is a growing need for water treatment technologies which focus removal of smaller particulate matter which is not always captured by traditional mechanical (e.g., filtration, floatation, etc.) and chemical means (e.g., utilizing coagulants and oxidizing agents) for water treatment.

Microplastics are often composed of synthetic polymer materials such as polyethylene, polystyrene, and elastomers like polyisoprene, all of which tend to resist biodegradation. Microplastics come in several shapes characterized as granular, fragment film, resin pellets, foam, and the most abundant, fiber, which is most often derived from the discharge of domestic washing machines containing the synthetic polymers for clothing. These particles include primary and secondary classifications, wherein primary microplastics are engineered to be small microbeads used in cosmetic, medicinal and industrial products like laundering textiles, while secondary microplastics are derived from the environmental breakdown of large plastics.

The aforesaid global and local developments are stirring interest and concern amongst numerous governmental and regulatory bodies and authorities. One such example is the Texas Commission on Environmental Quality's 2021 revisions to that state's water quality standards, which includes revisions to pH screening procedures and new prohibitions included in wastewater permits for facilities handling particular plastics.

The chemical composition of these synthetic plastics often also contains additives for protection from oxygen degradation and plasticizers for maintaining flexibility. These materials and the chemical makeup of other small anthropogenic litter, such as particles, pellets, and microbeads, lead to an extractive loss of plastics from wastewater treatment. While some tertiary treatments like membrane bioreactors, rapid sand filters, and disc filters might remove a portion of microplastics from treated wastewater effluent, there often remains trace amounts of such microplastics in the treated wastewater effluent leaving treatment facilities. Thus, microplastics continue to evade mechanical and chemical treatment processes and subsequently pollute terrestrial and marine ecosystems.

The development of technology which successfully detects and filters out such pollutants would not only contribute to the much-needed reusable water supply, but would also provide scientists and researchers the opportunity to study local environmental hazards and the impact of microplastics on nearby homeostatic systems. Furthermore, addition of technologically feasible enhancements to current resource recovery (e.g., wastewater treatment) facilities would enable existing facilities to more efficiently and completely remove microplastics from water and, thereby substantially reduce the need to construct less efficient and costly water treatment facilities.

SUMMARY OF THE INVENTION

The present invention provides an energy efficient method and automatic system for monitoring and size exclusion filtration of suspended particulates such as, without limitation, microplastics, from treated wastewater both downstream from and upstream of current physical and biological treatment processes. One benefit of the present invention is the easy access to microplastic samplings for inspection and maintenance of treated effluent.

The present invention improves the efficiency and sustainability of current wastewater treatment plants, improves the condition of receiving streams or water bodies and their ecosystems, ensures appropriate code compliance thereby avoiding costly penalties, and may facilitate the reuse of wastewater that is typically otherwise rich in nutrients and beneficial chemicals, thus providing the potential to generate additional resources and revenue for wastewater treatment plants.

A water sampling mechanism is provided for determining the presence of solids in water by continuous and passive monitoring and collection of water for analysis. More particularly, the water sampling mechanism comprises: an intake pipe which provides diverted flowing water from a source for monitoring and sampling, wherein the intake pipe includes an inlet and an outlet; an automatic sampler in direct or indirect fluid communication with the intake pipe for collecting one or more samples of the water flowing through the intake pipe, either at predetermined time intervals, or when triggered to do so by receiving a signal, or both; a sensor attached on or proximate to the intake pipe at a position upstream of the automatic sampler and which is capable of continuous and passive monitoring of the water for the presence of solids and producing monitoring results comprising at least one solids value, and continuous and passive analyzing of the monitoring results, wherein analyzing comprises comparing the at least one solids value to a predetermined threshold value and, if the solids value is greater than the predetermined threshold value, providing the signal to the automatic sampler to collect one or more samples of the water.

In some embodiments, water is wastewater produced by a manufacturing facility or wastewater treatment facility, and the solids are microplastics.

The sensor may comprise a total suspended solids sensor which includes a light source for passively detecting the presence of solids in the water. The predetermined threshold value is a baseline value equal to an expected solids value for the water which is determined based on the source of the water.

A solids monitoring and separation mechanism is also provided for facilitating visual determination of presence of solids in water and separating at least a portion of the solids from the water. More particularly, the solids monitoring and separation mechanism comprises: a conveyance pipe which provides diverted flowing water from a source for monitoring and sampling; a channel bay having and inlet, a sediment and powder bay positioned distally from the inlet, and an outlet positioned downstream of the sediment and powder bay, wherein the channel bay receives and channels the diverted flowing water, from the conveyance pipe, through the inlet, through the sediment and powder bay, and then exit through the outlet; a capture net which is positioned proximate to and in fluid communication with the inlet of the channel bay to receives the diverted flowing water and captures and separates at least a portion of solids from the diverted flowing water, the capture net including at least one compartment which includes a mesh having aperture size selected to capture and separate a desired size fraction of microplastics from the diverted flowing water; wherein the sediment and powder bay is further positioned in the channel bay distally from and downstream of the capture net and allows the flowing water to slow, after leaving the capture net and before exiting the channel bay, which facilitates conglomeration and separation of solids from the flowing water after flowing through the capture net, thereby increasing visibility of conglomerated and separated solids and further enabling visual detection of solids present in the diverted flowing water.

The sediment and powder bay may comprise one or more baffles for further slowing the flow of the flowing water, further facilitating at least a portion of solids present in the flowing water, after flowing through the capture net, to conglomerate and separate from the flowing water, thereby further increasing visibility of conglomerated and separated solids and further enabling visual detection of solids present in the diverted flowing water.

In some embodiments, the water is wastewater produced by a manufacturing facility or wastewater treatment facility, and the solids are microplastics.

In some embodiments, the capture net may comprise at least an upper compartment and a lower compartment, wherein the upper compartment comprises a first coarse mesh for capturing and separating larger sized solids, and the lower compartment comprises a second finer mesh for capturing and separating smaller sized solids, and wherein the diverted flowing water flows sequentially through the upper compartment first, then through the lower compartment, and into the downstream sediment and powder bay.

In some embodiments, the solids monitoring and separation mechanism may further comprise a tube positioned within the capture net and have an inlet connected to and in fluid communication with the inlet of the channel bay for receiving diverted flowing water and an outlet allowing the diverted flowing water to exit the tube, wherein the tube includes a diffuser feature through which at least a portion of the diverted flowing water flows before exiting the tube. In some embodiments, the diffuser feature of the tube comprises a plurality of apertures position on a ventral portion of the tube. Furthermore, the tube may have a covering attached thereto and comprising a fine solids capture filter having apertures of size from about 200 microns to about 500 microns for capturing and separating smaller solids from the diverted flowing water as it flows through the tube.

A water monitoring, sampling, and separation system is also provided which comprises the above-described water sampling mechanism and the above-described solids monitoring and separating mechanism, arranged in series with one another.

A method is provided for continuous and passive monitoring and sampling of water to detect the presence of solids, the method comprising the steps of: providing flowing water from a source to the intake pipe of the water sampling mechanism described above, wherein the water is wastewater produced by a manufacturing facility or wastewater treatment facility and the solids comprise microplastics; and recycling at least a portion of the flowing water back to the source.

A method is provided for monitoring, detecting and separating solids from water, the method comprising the steps of providing flowing water from a source to the conveyance pipe of the solids monitoring and separation mechanism of claim 11, wherein the water is wastewater produced by a manufacturing facility or wastewater treatment facility and the solids comprise microplastics; and recycling at least a portion of the flowing water back to the source.

A method is also provided for monitoring, sampling, and removing solids from water, the method comprising the steps of: providing flowing water from a source to the inlet of the intake pipe of the above-described water sampling mechanism; providing the diverted flowing water which exits the outlet of the intake pipe to the conveyance pipe of the above-described solids monitoring and separation mechanism, and recycling at least a portion of the flowing water back to the source, wherein the water is wastewater produced by a manufacturing facility or wastewater treatment facility and the solids comprise microplastics.

BRIEF DESCRIPTION OF THE DRAWINGS

The foregoing summary, as well as the following detailed description of the invention, are better understood when read in conjunction with the appended drawings. For the purposes of illustrating the invention disclosed and contemplated herein, exemplary embodiments are shown in the drawings, in which the details of known and conventional features or apparatus may not be specifically shown but are nonetheless reasonably understood and expected to be present. It is further noted that the figures and individual features shown therein may be schematic and, therefore, not drawn to scale. Descriptions provided for elements and features which are shown and identified using a numeral in the figures are applicable, unless otherwise indicated, to those and analogous elements and features shown and identified by those same numerals in any subsequent figure.

FIGS. 5-6 show longitudinal cross-sectional views of the plastic pellet, and powder capture net apparatus of FIGS. 3-4, which more clearly show the arrangement of its interior elements, including separation devices and a diffuser, therein.

DETAILED DESCRIPTION

Figure 1:
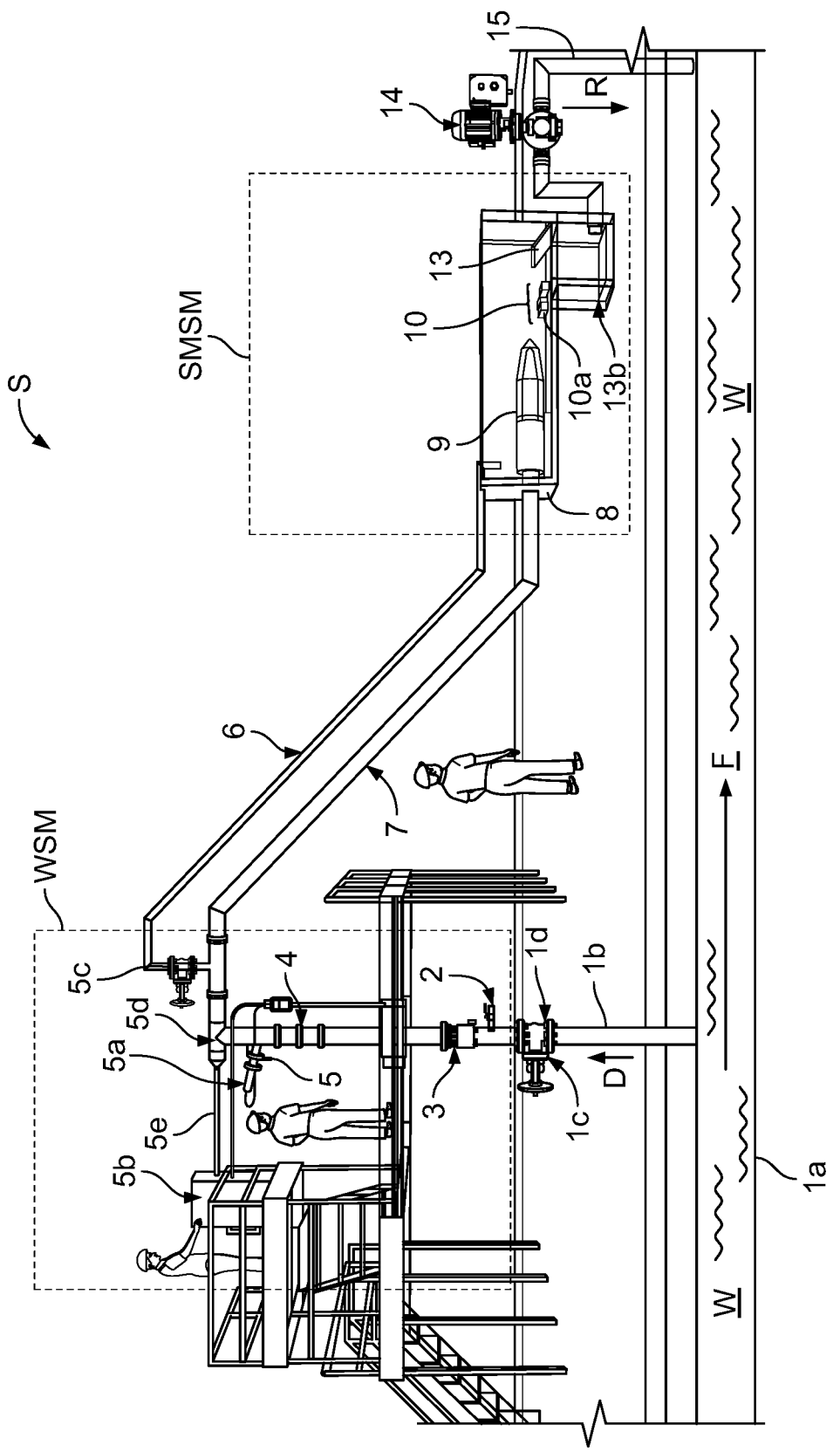
FIG. 1 shows a schematic macro view of an exemplary embodiment of a wastewater sampling system in accordance with the present description and having a wastewater sampling mechanism and solids monitoring and separation mechanism, wherein treated wastewater effluent is diverted from a main line, through the wastewater sampling mechanism and, thereafter, through the solids monitoring and separation mechanism.

General and specific embodiments of methods, apparatus, and systems for detecting and removing microplastics from water will now be described. It should be understood that, although the methods, apparatus, and systems described herein are applied to detecting and removing microplastics from wastewater, particularly from treated wastewater effluent produced by wastewater treatment plants, the illustrated embodiments are exemplary only and should not be taken as limiting the scope of the invention. For example, the methods, apparatus, and systems described and contemplated herein may be applied to treat water from virtually any source (e.g., polluted surface water, run off from industrial sites, municipal drainage, etc.), as well as prior to, or at any of several points during, treatment of wastewater by other processes and methods.

Additionally, while the methods, apparatus, and systems described herein are applied for detecting and removing microplastics, it will be recognized and understood by persons of ordinary skill in the relevant art that they may also, or alternatively, be applied for detecting, separating, removing, or some combination of these, other substances or contaminants which are present in an aqueous media and have characteristics similar to those of microplastics, such as other solids having sizes small enough to be suspended in an aqueous medium and escape detection and separation by other separation technologies and methods.

Modern wastewater treatment plants generally apply sophisticated physical and biological treatment processes and methods, including pre-treatment dissolved air flotation devices and various other removal mechanisms intended to rid wastewater of various impurities, including microplastics. However, the current methods and systems remain flawed and often incapable of detecting and removing some of the smaller contaminants, such as microplastics, or are incapable of detecting and removing sufficient quantities of such contaminants. Researchers and environmental engineers continue to detect and identify microplastics in unacceptable quantities in treated wastewater effluent, even after treatment by several of the aforesaid sophisticated physical and biological treatment processes and methods. Current primary, secondary, and tertiary treatment processes often fail to remove certain particulate matter from wastewater effluent due to its size, chemical composition, and inefficient separation methods.

As used herein, "microplastics" means pieces and fragments of plastic material having sizes less than about 5 millimeters (mm), such as, without limitation, as small as about 1 micron or even as small as about 0.1 micron or greater. Microplastics exist in different sizes and shapes such as, without limitation pellets, flakes and powders. Pellet microplastics are generally sized from about 1.5 mm to about 5 mm in their largest dimension (i.e., at least one of the length, width, and thickness of a microplastics pellet is 1.5 mm to about 5 mm, with the remaining dimension being equal to or smaller), while powder microplastics are generally about 500 microns or less in average diameter. Microplastics flakes are recognized by their irregular shapes, rather than their size and, therefore, may be any size from about 5 mm and less.

Microplastics include such plastics fragments regardless of whether they have been released directly into the environment (i.e., "primary" microplastics) or formed indirectly in the environment (i.e., "secondary' microplastics) such as through decay or degradation (which tends to occur slowly), whether by physical, mechanical, chemical, or radiation exposure mechanisms. While the present disclosure generally concerns microplastics present in water sources and wastewater, microplastics may be found in any environmental media, including water, soil, and air, and may also migrate or be transported between such media.

In general, effluent limitations for plastics in treated effluent from a wastewater facility in the United States have not been regulated specifically. Rather, they are regulated indirectly and lumped with other pollutants as part of the wastewater permit condition described therein mainly as "floating solids or foams." The effluent limitation for floatables (which includes plastics and microplastics as currently defined in such permits and regulations) is typically rather vague in most permits and simply defined as "no discharges of floating solids or foams other than trace amounts." As a result, what occurs in plastic manufacturing facilities is that their wastewater treatment processes are equipped with the typical dissolved air flotation and baffle systems which typically adequately address floating solids and foams together as a group or "package," but are typically incapable of capturing and removing microplastic solids from such wastewater streams.

Accordingly, it has been found that microplastics bypass or overload many of the aforesaid systems and processes designed to address typical floating solids and foams, but which are not designed or effective to address microplastics. The invention described and contemplated herein is capable of detecting and capturing microplastics effectively from water streams, such as treated wastewater effluent produced by plastics manufacturers and wastewater treatment facilities, by using a series of mechanisms which can operate individually, but also cooperate and overlap somewhat redundantly with one another, to provide extremely efficient detection and removal of microplastics. Microplastics have unique physical characteristics which means they cannot be lumped together with typical floatable solids and foams with the expectation that technology which removes typical floatable solids and foams will also remove microplastic solids. They simply do not. For example, without limitation, microplastics powders have physical properties which cause them to aggregate or conglomerate together in stagnant or relatively low turbulence conditions. Microplastics also generally tend to float on the surface of water under similar conditions. Additionally, microplastics tend to have an affinity for and stick to solid surfaces such as the walls of pipes, containers, etc. A useful optical property of microplastics is their ability to reflect light, rather than simply scatter or absorb light as some other types of solids which may be present in wastewater.

One aspect of the invention described and contemplated herein takes advantage of the one or more of the aforesaid physical properties of microplastics (e.g., tendency to aggregate and ability to reflect light) to visually identify the microplastics in wastewater by using a total suspended solids (TSS) sensor. Passing light through the water, such a sensor identifies the microplastics (by reflecting and scattering the light), producing a signal and then activating a signal to automatically collect a wastewater sample for further analysis and characterization. Another of aspect of the invention described and contemplated herein enables an operator or other user to physically look at the treated wastewater through a visual solids detection device, such as a sight glass, and decide whether plastic pellets or other microplastics are visible and likely present in the wastewater and, if so, take a manual sample of the wastewater for further analysis and characterization. Since microplastics are generally visible to the naked eye, such features for enabling manual visual detection of microplastics present in wastewater while flowing in a pipe or other conduit may be beneficial.

Finally, as described in detail below, still another aspect of the invention described and contemplated herein provides a very efficient capture net which may be designed with multiple sections or compartments and optional features which cooperate to successively and efficiently trap, capture and separate different size fractions of microplastics (e.g., one or more of pellets, flakes, and powder), resulting in a passive but effective device and process which enable monitoring, identifying and also removing microplastics from the wastewater.

The mechanisms and methods described and contemplated herein have not previously been developed and combined for use a remote and automated process which effectively monitors and removes plastics without blocking or plugging the monitoring and removal system. The wastewater monitoring, sampling, and removal system described and contemplated herein for detecting and removing microplastics can be monitored and operated continuously, 24 hours per day, 7 days per week, and even 365 days per year without an operator, monitor or other user physically present onsite with the system. Periodic collection and replacement of automatic sampling containers (e.g., about 24 1-L bottles) and visual confirmation of the presence of microplastic once the samples from the automatic sampler or from the net are the main activities requiring regular, periodic operator action.

A primary object of the present invention is to provide methods, apparatus and systems capable of detecting and retaining (e.g., separating and/or removing) microplastics from treated wastewater at a variety of wastewater management plants. It is another object of the wastewater sampling mechanism to provide a technologically feasible and efficient method for monitoring the presence of microplastics in treated wastewater effluent without the need for extensive labor.

It is another object of the wastewater sampling mechanism to provide automated and continuous monitoring for microplastics, such as powders, pellets, and flakes, in treated wastewater. It is another object of the wastewater sampling mechanism to capture solids for the study and subsequent enhancement of wastewater plant treatment methods, including providing the ability to discover real-time potential problems at a wastewater plant and at manufacturing and product handling units as real-time data may be stored and retrieved over time.

It is another object of the wastewater sampling mechanism to capture solids for the study of region and industry-specific origin of microplastic infiltration sources for the plastic of treated wastewater effluent.

The invention described and contemplated herein permits visual and morphological inspection of treated wastewater for remaining microplastics. The present invention is designed such that the monitoring of treated wastewater for remaining microplastics remains uninterrupted, thereby removing a need for constant human monitoring and intervention. At the same time, the present invention collects microplastics from treated wastewater effluent in a manner permitting manual human selection of residual microplastics due to the redundant yet efficient wastewater sampling mechanism's collection configuration. Automatic operation of the present invention may be monitored remotely designated individuals and/or at least one wastewater treatment plant automated computer system.

Other features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

With reference to FIGS. 1-4, an exemplary wastewater monitoring, sampling, and removal system (S) in accordance with the invention described and contemplated herein is shown. More particularly, in this exemplary embodiment, the wastewater monitoring, sampling, and removal system (S) includes a wastewater sampling mechanism (WSM) and solids monitoring and separation mechanism (SMSM) arranged in series. As described in detail below, treated wastewater effluent (W) is diverted from a main line 1a, by an intake pipe 1b, and provided to the wastewater sampling mechanism WSM and, thereafter, through the solids monitoring and separation mechanism SMSM. As described below, this diversion of the treated wastewater effluent from the main line 1a to the wastewater sampling mechanism WSM facilitates at-will sampling and continuous monitoring for the presence of microplastics in the treated wastewater effluent.

It is noted that the source of the water or wastewater (W) provided to the wastewater monitoring, sampling, and removal system (S) through the main line 1a is not particularly limited and may be from any source such as, without limitation, a plastics manufacturing facility's process wastewater effluent, whether treated or not, or any wastewater treatment facility or system, or water captured from some other source, whether treated or not. The exemplary embodiment described herein contemplates a plastic manufacturing facility as the source of treated wastewater effluent (W)

provided by the main line 1a. It is also noted that the wastewater to be monitored and sampled and that is provided to the system (S) need not be provided by a main line or other pipe or conduit, but rather may be provided by any means or device suitable to the source. For example, without limitation, where polluted surface water is to be monitored and sampled by using the system (S), the wastewater may be provided or otherwise provided from a stream or other body of water.

Figure 2:
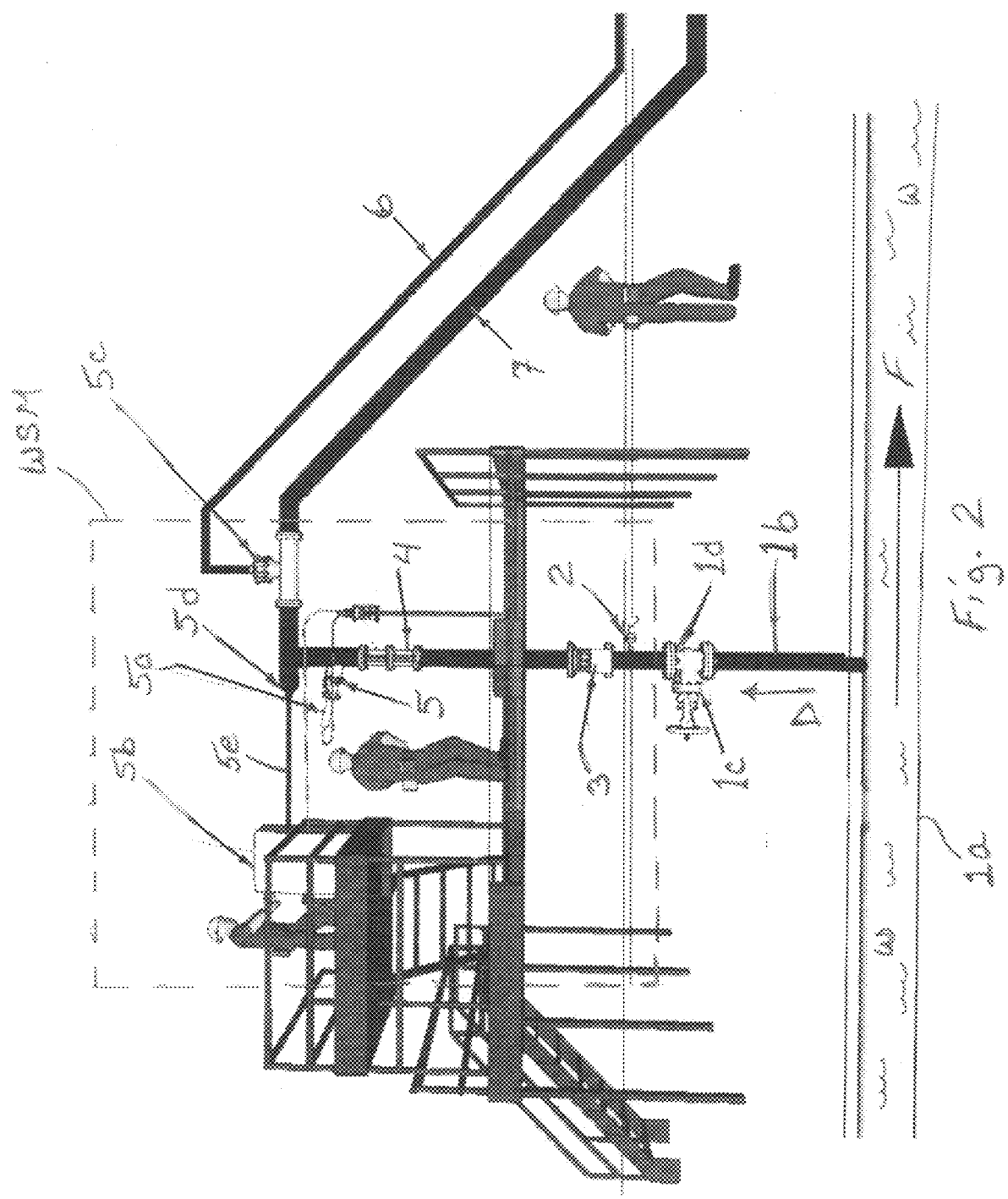
FIG. 2 shows a schematic view of a first phase of the system of FIG. 1, including the main line, diversionary effluent intake pipe and water sampling mechanism where initial visualization of solids, such as microplastics, and wastewater sample collection occur.

More particularly, in the exemplary system (S) shown in FIGS. 1-2, a wastewater treatment main line 1a provides treated wastewater (W) which flows therethrough, as shown by the arrow (F). The system (S) also typically includes an intake pipe, such as the effluent intake pipe 1b shown in FIGS. 1-2, which is mechanically attached to and in fluid communication with the main line 1a, for receiving and directing at least portion of wastewater (W) diverted from the main line 1a therethrough, in the direction of the arrow (D). In one embodiment, main line 1a is in fluid communication with effluent intake pipe 1b via an at least 10.16 centimeter (cm) (i.e., four (4) inches) to an at least 20.32 cm (i.e., eight (8) inches) inner diameter redactor (not shown per se), wherein the redactor dimensions facilitate pressurized pipe mechanics to carry effluent inflow from main line 1a, through the intake pipe 1b, to the upstream wastewater sampling mechanism WSM. In the exemplary embodiment shown in FIG. 1, the effluent intake pipe 1b is attached to the main line 1a at a position downstream of treatment processes and methods applied to the wastewater, so that the wastewater effluent received and flowing through the effluent intake pipe 1b has been treated and is, therefore, treated wastewater effluent.

As will be recognized by persons of ordinary skill in the relevant art, in some embodiments, the intake pipe 1b may be attached to the main line 1a upstream of and before all treatment processes and methods are applied to the wastewater, so that the wastewater received and flowing through the intake pipe 1b has not yet been treated and is, therefore, untreated wastewater. In still other embodiments, the intake pipe 1b may be attached to the main line 1a at any point among the treatment processes and methods which are applied to the wastewater, so that the wastewater received and flowing through the intake pipe 1b has been partially treated and is, therefore, partially treated wastewater and the intake pipe 1b may be considered an effluent intake pipe 1b.

The system (S) may further include a shut off valve 1c, which is mechanically attached to and in fluid communication with the effluent intake pipe 1b, for allowing wastewater to flow therethrough, from the main line 1a. The shut-off valve 1c also enables manually shutting off that flow for maintenance or emergency purposes. The shut-off valve 1c can be any type of valve suitable and capable of the foregoing operation such as, without limitation, a gate valve, a globe valve, and the like.

The system (S) may further include a flow regulator valve 1d, which is mechanically attached and in fluid communication with effluent intake pipe 1b, for regulating the quantity or volume of wastewater effluent flowing into the effluent intake pipe 1b from the main line 1a and being transported and provided to a water sampling mechanism which is described in detail below. The flow regulator valve 1d may be any type of flow regulator suitable and capable of the foregoing operation such as, without limitation, an actuator, a butterfly valve operated with an actuator, and the like.

As can be seen in FIGS. 1-2, the system (S) includes a water sampling mechanism WSM, the components of which are generally encompassed by the dotted box (WSM) and will now be described. The water sampling mechanism WSM generally incorporates modified wastewater treatment instrumentation, including at least remote environmental monitors, various aquatic samplers and other automatic sampling mechanisms, and numerous capture mechanisms for monitoring the presence of microplastic pellets and powders in the treated effluent.

In some embodiments of the wastewater monitoring, sampling, and removal system (S), the wastewater sampling mechanism WSM is in direct fluid communication with wastewater treatment main line 1a. In another embodiment of the present invention, which is shown in FIGS. 1-2, the wastewater sampling mechanism WSM is in fluid communication with the wastewater treatment main line 1a indirectly via effluent intake pipe 1b. The wastewater sampling mechanism WSM includes at least two sampling components which enable and facilitate iterative monitoring and sampling of wastewater effluent, as described hereinbelow. In another embodiment, effluent sampling and monitoring is conducted inside a wastewater sampling mechanism shelter (not shown per se) for housing an at least one above-ground wastewater sampling mechanism.

As also shown in FIG. 1, the system (S) may further include a manual sample collection valve 2 which is mechanically attached and in fluid communication with the effluent intake pipe 1b. The manual sample collection valve 2 facilitates manual collection of one or more wastewater samples, at any time, from wastewater passing through the effluent intake pipe 1b. Such wastewater samples may be visually inspected by a user or operator of the system (S) for morphological detection (i.e., based appearance of the wastewater sample) of microplastics, as well as for ongoing mechanism functionality.

It is noted that the condition and content of the wastewater samples collected at the manual sample collection valve 2 will be essentially the same as for the wastewater in the main line 1a at that point in the treatment process where the effluent intake pipe 1b is attached to the main line 1a. For instance, in the embodiment shown in FIG. 1, the condition and content of one or more wastewater samples manually collected at the manual sample collection valve 2 will be essentially the same as the effluent wastewater in the main line 1a at the point where the effluent intake pipe 1b is attached to the main line 1a.

In some embodiments, the system (S) includes a flow meter 3 which is mechanically attached to or otherwise integrated with the effluent intake pipe 1b for measuring the flow of wastewater through the effluent intake pipe 1b. The flow meter 3 may, for example without limitation, be attached to the effluent intake pipe 1b adjacent or otherwise proximate to the manual sample collection valve 2 or the flow regulator valve 1d. The purpose of measuring the flow of the wastewater is to maintain the operability of the system (S) and may assist in optional load calculation.

The flow meter 3 may be any be any type of flow meter or velocity sensor suitable and capable of the foregoing operation such as, without limitation, a magmeter 3. A magmeter measures flow of the wastewater based on voltage created as the wastewater effluent (a conductive liquid) flows through a magnetic field created by energized coils arranged outside the pipe 1b. Thus, such flow sensors generally avoid or minimize direct contact between the flow measuring device and wastewater flowing through the effluent intake pipe 1b which, in turn, minimizes potential maintenance issues by allowing the sensors to be located outside the pipe.

In some embodiments such as that shown in FIG. 1, the water sampling system WSS of the wastewater monitoring, sampling, and removal system (S) may also include a visual solids detection device, such as a transparent sight glass 4, which is mechanically integrated into the effluent intake pipe 1b and equipped with tubular lighting to facilitate visual identification of microplastics. The sight glass 4 enables viewing the wastewater flowing through the effluent intake pipe 1b such as by an operator or other user of the system S. When visual inspection of the wastewater effluent through the sight glass 5 indicates the presence of microplastics, one or more samples of the wastewater effluent may be manually collected by an operator or other user by using the manual sample collection valve 2.

As shown in the exemplary embodiment of FIGS. 1-2, the wastewater sampling mechanism WSM of the wastewater monitoring, sampling, and removal system (S) may further include a sensor mounting device, such as the total suspended solids (TSS) sensor mounting device 5 shown in the figures, and a sensor, such as the TSS sensor 5a shown in the figures, which are mechanically attached to the effluent intake pipe 1b and capable of monitoring and detecting the presence of microplastics in wastewater flowing through the intake pipe 1b. The TSS sensor 5a includes a light source for passive detection of solids and may be connected to the intake pipe 1b at a location downstream of the manual sample collection valve 2 and velocity sensor 3.

The type of TSS sensor 5 is not particularly limited, as long as it is capable analyzing water for turbidity without physical contact with the water and is properly calibrated, as follows. In an exemplary embodiment, the TSS sensor 5a detects the presence of microplastic solids (e.g., particles, powders, flakes, etc.) in the treated wastewater effluent in the intake pipe 1b through the emission of a light beam through the wastewater, followed by determining whether the light indicates (e.g., based on degree of turbulence) the presence of microplastic solids in the wastewater and whether there is a sufficient amount of microplastic or solids to warrant sampling. Due to the occurrence of biofouling, which is expected in a typical treated wastewater stream and associated wastewater handling equipment, it is beneficial for the TSS sensor 5a to include a wiper system (not shown per se) which periodically cleans the face of the sensor component (not shown per se) of the TSS sensor 5a. While not critical, a TSS sensor 5a which includes a wiper system will provide more accurate TSS readings over longer periods of time and proves to need less cleaning than with a TSS sensor 5a without a wiper system.

In some embodiments, the wastewater sampling mechanism WSM may include an all-weather refrigerated portable automatic sampler 5b for sampling treated wastewater effluent when specified preset conditions are met. The TSS sensor 5a is in electrical communication with the all-weather refrigerated portable automatic sampler 5b for providing a signal to the sampler 5b to cause the sampler 5b to collect one or more discrete effluent samples from the treated wastewater effluent.

As will be understood by persons of ordinary skill in the relevant art, the TSS sensor 5a system is calibrated by assuming or providing a baseline value of expected solids (e.g., degree of turbulence) in the treated wastewater effluent, and then comparing the solids reading (e.g., actual turbulence reading) to a predetermined threshold value for triggering automated wastewater sampling. Once that threshold value trigger is reached, the TSS sensor 5a transmits a signal that is codified to the automatic sampler 5b to collect a sample. As will be understood and readily practicable by persons of ordinary skill in the relevant art, the threshold value is determined based on the source of the wastewater and any known treatments to which the wastewater has been subjected.

In some embodiments, an automatic wastewater sampling port 5d is provided in fluid communication with the intake pipe 1b or a diversion line 5e which branches off and draws wastewater effluent from the intake pipe 1b. The all-weather refrigerated portable automatic sampler 5b extracts one or more wastewater effluent samples, from the wastewater effluent traveling through the intake pipe 1b or diversion line 5e via sampling port 5d, in volumes dependent on electrical signals from upstream TSS sensor 5. In one embodiment, all-weather refrigerated portable automatic sampler 5b is configured and equipped for, and may be programmed to, collect up to, for example without limitation, about twenty-four (24) 1-liter samples of wastewater effluent before reloading the sampler tb with empty 1-liter collection vials is necessary. The number of volumes and samples to be automatically collected by the automatic sampler 5b may be predetermined and selected during the initial testing and calibration of TSS sensor 5a and associated apparatus (e.g., TSS sensor 5a, sampler 5b, etc.). In another embodiment, a wastewater treatment monitor or other user may re-program the volume and number of samples of wastewater effluent to be extracted (collected) from the wastewater effluent by the all-weather refrigerated portable automatic sampler 5b. The automatic sampler 5b may be also programmed to take samples from the diversion line 5e at a programmed time or time interval each day, or on selected days, without using or otherwise involving the TSS sensor 5a, or even in combination with collecting samples when triggered by a signal from the TSS sensor 5a.

Thus, as mentioned above, the wastewater sampling mechanism WSM includes two wastewater sampling components which enable and facilitate iterative sampling and monitoring of wastewater effluent, as follows. A first wastewater sampling component (1), which is manually applied and operated, includes the sight glass 4 together with the manual sample valve 2. Together, these features allow an operator or other user to manually and visually detect the presence of microplastics in the wastewater flowing through the intake pipe 1b and manually take one or more samples.

The second sampling component (2) of the wastewater sampling mechanism WSM provides automated and continuous monitoring and sampling for microplastics and comprises the TSS sensor 5a and associated apparatus (e.g., TSS sensor 5a, sampler 5b, etc.). More particularly, as described above, the TSS sensor 5 and the automatic sampler 5b are configured and programmed to automatically and remotely monitor the wastewater for the presence of microplastics and operate to collect one or more wastewater samples for analysis. As described above, when wastewater effluent contains solids particles which create turbidity and, under such conditions, the particles scatter a beam of light which is directed by the TSS sensor 5a through the wastewater, and a signal is sent by the TSS sensor 5a to the calibrated TSS sensor 5. If the aforesaid predetermined threshold value (e.g., a turbidity value) is exceeded, then a signal is sent to the automatic sampler 5b to collect one or more wastewater samples. In some embodiments, the sample(s) may be stored in a refrigerated chamber (not shown per se) until an operator or other user comes to collect them. The chamber may, for example, have capacity to hold about 24 1-L sample bottles.

It noted that, as will be recognized and appreciated by persons of ordinary skill in the relevant art, the TSS sensor 5 generally not only detects microplastic solids, but also other solids which may be present in the wastewater being monitored, which has the potential to confuse the microplastic solids (powder) with other solids. However, by implementing the above-described calibration process which includes providing or setting a predetermined threshold value for the wastewater effluent that accounts for expected presence of other solids (i.e., an expected degree of turbidity) in the effluent from the wastewater monitoring, sampling, and removal system (S), this second sample component (2) of the wastewater sampling mechanism WSM is configured and able to detect ("see") beyond the expected baseline solids in the treated wastewater effluent being monitored and sampled. This calibration process and resulting configuration of the TSS sensor 5 and TSS sensor 5a particularly enable this sample component (2) of the wastewater sampling mechanism WSM to monitor and detect, specifically, the presence of microplastics in wastewater, aside from and in addition to the possible presence of other solids in the wastewater.

Biofouling of piping and peristaltic pump may be reduced or avoided through programming the all-weather refrigerated portable automatic sampler 5b to capture and release wastewater effluent samples at least once daily or at any other time or time interval, irrespective of a triggering event occurrence, to ensure the wastewater sampling mechanism WSM system remains flushed, however, such samples also be used as monitoring samples for analysis.

Wastewater effluent samples may, for example without limitation, be collected or removed from the wastewater sampling mechanism WSM using the diversion line 5e, which is in fluid communication with at least sampling port 5d. Such a diversion line 5e may suitably be have an inner diameter of from about 127 mm (i.e., 0.5 inch) to about 254 mm (i.e., 1 inch). In another embodiment, wastewater effluent samples may be transported from the wastewater sampling mechanism WSM using a plurality of vials. In another embodiment, a biofouling avoidance method and system may include the integration of a plurality of pressure indicators (not shown) and at least one regulator valve (not shown) for the reading of and possible regulation of effluent flow between the TSS sensor 5 and the all-weather refrigerated portable automatic sampler 5b.

In another embodiment, biofouling may be further prevented by the placement of the all-weather refrigerated portable automatic sampler 5b at a higher elevation than effluent sampling port 5d. For example, by positioning the peristatic pump (not shown, since it is typically located at least partially within the automatic sampler 5b) at an elevation which is a distance above the diversion line 5e, wherein the distance is about 5 to 10 times the diameter of the diversion line 5e, which minimizes or avoids water accumulation and biofouling of the diversion line 5e. In yet another embodiment, the all-weather refrigerated portable automatic sampler 5b is installed to ensure system chill, thereby decreasing chances of bacterial growth in the wastewater sampling mechanism and its sampling components.

Figure 3:
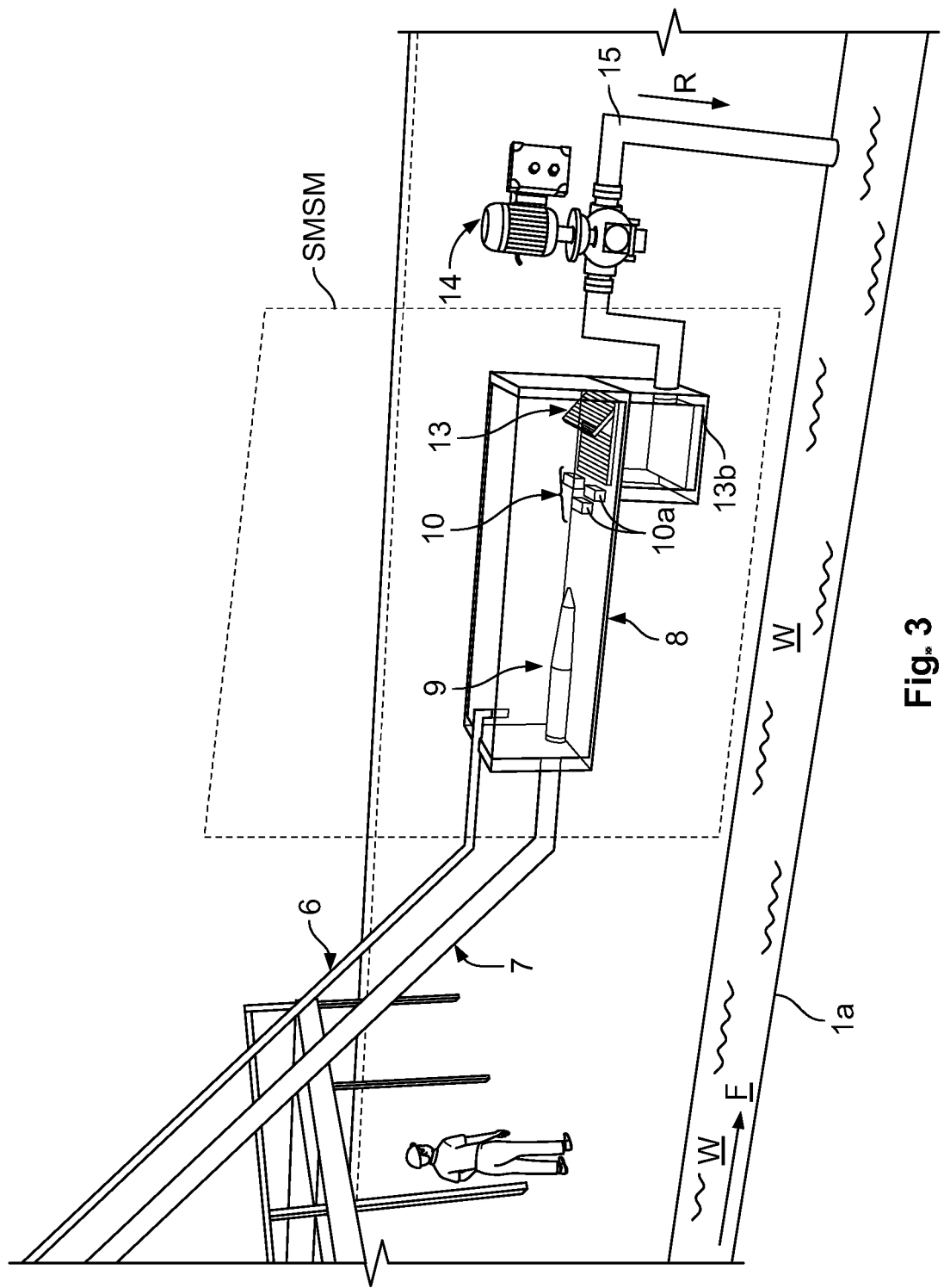
FIG. 3 shows a schematic view of a second phase, or latter portion, of the system of FIG. 1, including the various components of the solids monitoring and separation mechanism, such as an exemplary embodiment of a suspended plastic pellet, and powder capture net apparatus.

As can be seen most clearly in FIGS. 1-3, the wastewater monitoring, sampling, and removal system (S) includes main sampling conveyance line 7, which is in fluid communication with the intake pipe 1b and the solids monitoring and separation mechanism SMSM, for conveying the wastewater effluent from the intake pipe 1b and wastewater sampling mechanism WSM to the solids monitoring and separation mechanism SMSM for continuous and passive monitoring and collection of wastewater samples, as well as capture and separation of solids, including microplastics, from the wastewater effluent. The main sampling conveyance line or pipe 7 may, for example, be from about 10.16 cm (i.e., 4 inches) to about 20.32 cm (i.e., 8 inches) in diameter.

A minimal drip line 6 is also provided in fluid communication with the intake pipe 1b and the channel bay 8. A manual valve 5c is provided in fluid communication with the minimal drip line 6 and may be adjusted on an as-needed basis to allow and convey minimal wastewater flow through the drip line 6 while providing an additional sample collection port for detection of microplastics in the wastewater. In another embodiment, the main sampling conveyance line or pipe 7 may facilitate fluid communication between the drip line manual valve 5c and the solids monitoring and separation mechanism SMSM for providing an additional multi-purpose sampling/capture port to facilitate monitoring and detection of microplastics.

Figure 4:
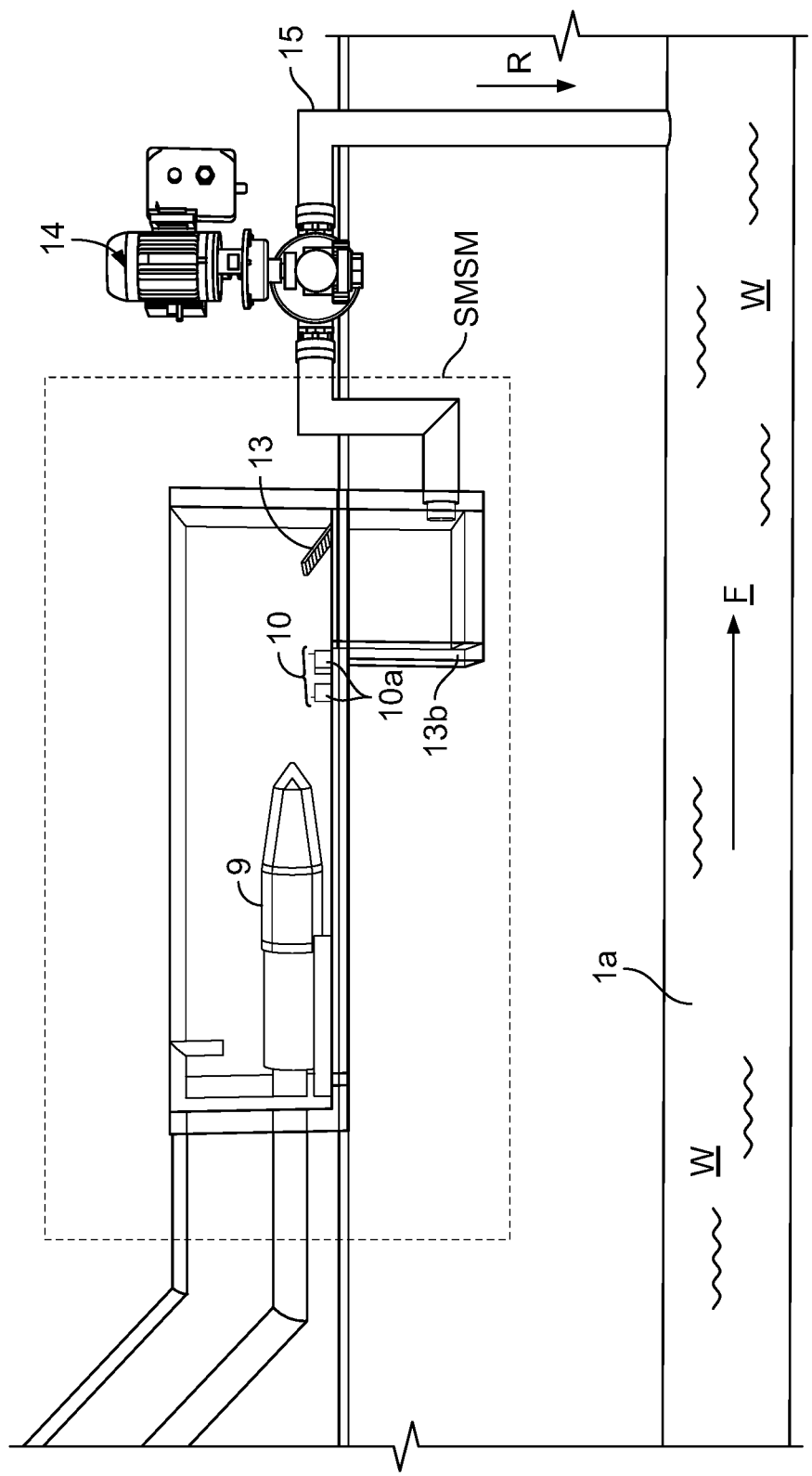
FIG. 4; shows a schematic elevated side view of the second phase of the system and the solids monitoring and separation mechanism of FIG. 3, including the plastic pellet, and powder capture net apparatus.

With reference now generally to FIGS. 1 and 3-4, the wastewater monitoring, sampling, and removal system (S) includes a solids monitoring and separation mechanism (SMSM), the components of which are generally encompassed by the dotted box (SMSM) and will now be described. The solids monitoring and separation mechanism SMSM comprises at least a plastic pellet and powder capture net (P3CN) 9. While the P3CN 9 is capable of capturing and separating solids of almost any kind, as described hereinbelow, the P3CN 9 is configured and operated to capture, separate and remove microplastics from water that currently manage to evade primary, secondary, and tertiary treatment processes typically included in water treatment processes and systems. In some embodiments of the system (S), after the presence of such microplastics has been monitored and detected both visually and morphologically (i.e., based on differences in the appearance and/or turbidity of wastewater), at least a portion of the microplastics may be passively and continuously captured and removed from the wastewater at least by operation of the P3CN 9, as will be described in detail below.

Generally, water to be monitored and treated, such as treated wastewater effluent flowing through the main line 1a of the system (S) of the embodiment shown in FIG. 1, is provided and funneled through the P3CN 9 in a continuous fashion for the retention of microplastic solids, including but not limited to pellets, flakes, and powder, in a passive form of capture achieving substantially complete removal of pellets in the P3CN 9. In some embodiments of the invention described and contemplated herein, the P3CN 9 may be monitored by on-site operators, or other users and staff, through basic visual and morphological inspection. Alternatively, or in addition, on-site operators, user, and staff may come at a later time to inspect, verify, and remove the captured and removed microplastics (or other solids, or both).

As shown in the exemplary embodiment of FIGS. 1 and 3-4, the solids monitoring and separation mechanism SMSM may further include a channel bay 8, which may be formed of concrete or other suitable water containment material and is fluidly connected to the main sampling conveyance line 7. In the foregoing arrangement, wastewater flows from the intake pipe 1b, through the wastewater sampling mechanism WSM and conveyance line 7 and into the channel bay 8.

The P3CN 9 is detachably disposed within the channel bay 8, for receiving and filtering wastewater provided from the conveyance line 7 (and from the minimal drip line 6, if present) to the channel bay 8. This fluid communication of components of the system (S) is an integral feature of the wastewater sampling system wherein microplastics are continuously filtered out of the treated wastewater effluent. During operation of the system (S) and the solids monitoring and separation mechanism SMSM, wastewater effluent continuously flows through the channel bay 8 and the P3CN 9 which passively performs the capture and removal of microplastics from the diverted treated wastewater effluent through a current- and size-based filtration process.

With reference now to the P3CN shown in FIGS. 1 and 3-6, the P3CN 9 accomplishes the capture, separation and removal from water (such as wastewater effluent) by size exclusion filtration. As used herein, "size exclusion filtration" means successive separation and removal of fractions or populations of differently sized solid particles from a fluid such as water or air, beginning with the largest sized solid particles and ending with the smallest sized solid particles to be separated. In the present case, size exclusion filtration is described as performed by the P3CN to capture and separate microplastics from water, such as wastewater and, particularly, treated wastewater effluent.

Referring now to FIGS. 5-6, P3CN 9 is comprised of at least one compartment which includes a mesh or other filter having aperture or pore size selected to capture and separate a desired size fraction of microplastics from the wastewater (W). In some embodiments, the P3CN may be comprised of at least two compartments, each of which includes a mesh or other filter having aperture or pore size having aperture or pore size, each of which is selected to capture and separate a different size fraction of microplastics from the wastewater (W). Of course, it should be understood that the P3CN may comprise more than two such compartments for capture and separation of more than two different size fractions of microplastics from the wastewater (W).

For example, in the exemplary embodiment shown in FIGS. 5-6, the P3CN is comprised of an upper compartment 9a and lower compartment 9b. The upper compartment 9a includes a first relatively coarse mesh having pores or apertures of size from approximately 1.5875 mm (i.e., 1/16 inch) to approximately 0.79375 mm (i.e., 1/32 inch) for capturing coarser microplastic pellets and broken pellets (i.e., which have size of about 0.79375 mm or greater, depending on the first mesh and its aperture size) from the treated wastewater effluent. The lower compartment 9b, on the other hand, includes a second smaller, finer mesh having pores or apertures of approximately 500 to 200 microns (or even smaller, finer mesh) that is designed to trap smaller microplastic powders (i.e., having sizes of about 200 microns or greater, depending on the second mesh and its aperture size).

Without intending to be limited, in an exemplary embodiment, after construction but prior to installation in the channel bay 8, the P3CN has the configuration of a generally rectilinear-shaped pouch. In such an exemplary embodiment, the upper compartment 9a is at least partially nested within the lower compartment 9b (see, e.g., FIGS. 5-6) and the pouch has a width of about 1.47 meters (i.e., 2 feet, 10 inches) and a length of about 4.82 meters (i.e., 15 feet, 10 inches).

Looking at FIGS. 3-6, and particularly at FIGS. 5-6, during operation of the system (S) and particularly of the solids monitoring and separation mechanism SMSM, wastewater (W) flows into the center of the P3CN 9, from line 7, and first encounters the upper compartment 9a which has the first coarser larger mesh for filtering and separating larger, coarser microplastic particles first, and then the wastewater (W) encounters and flows through the lower compartment 9b which has the second finer mesh for filtering and separating smaller, finer microplastic particles.

Especially, but not only, for embodiments of the P3CN 9 which comprise more than one mesh compartment for capturing and separating different size fractions of microplastics as described above, each such mesh compartment may include a cutting guide line for providing an operator or user with a location at which to cut each mesh compartment, thereby enable the removal and examination of each size fraction of microplastics captured by the P3CN 9. For example, as shown most clearly in FIGS. 5 and 6, each of the upper and lower mesh compartments 9a, 9b may include a cutting guide line L1, L2, respectively, to indicate to an operator or other user where to cut each mesh compartment for removal and examination of each size fraction of microplastics captured by the P3CN and by each compartment 9a, 9b.

The foregoing design facilitates operation of the P3CN 9 and recovery of both pellet and powder microplastic size fractions easily and in a clean and swift operation. The P3CN 9 is easily attached to the main sampling conveyance line 7 with a mechanical mounting system 9 (not shown per se). The solids monitoring and separation mechanism SMSM both monitors wastewater in the system (S) for the presence of microplastics, and also removes essentially all of the microplastic pellets from the wastewater (W), thus operating as an efficient monitoring and separation mechanism for that fraction of microplastics (i.e., pellets).

In some embodiments, one or more tubes 11 having a diameter of at least about 10.16 cm (i.e., about four inches) and, optionally, a diffuser feature, such as a plurality of apertures or openings 11 of any shape (i.e., circular, linear or curved slots, "x" s, etc.). The diffuser feature dampens and distributes the flow of the wastewater (W) and the microplastics present therein. In some embodiments such as that shown in the figures herein, the diffuser feature of the tubes 11 may comprise a plurality of circular apertures 11a, each having a diameter of about 2.54 cm (i.e., one inch) diameter. The tube 11 may be embedded within P3CN for additional separation and capture of finer microplastics (e.g., powder). The tube may, for example without limitation, be made of stainless steel, poly(vinyl)chloride plastic (PVC), rubber, or similar material). Additionally, the tube 11 may be covered with a 500- to 200-micron mesh 12. When covered in such a mesh, this tube 11 provides an additional mechanism which enables the P3CN to capture and remove of pellet, flake, and powder forms of microplastics from the wastewater (W) flowing through the tube 11, thereby operating as an efficient mechanism for the removal of all microplastics.

In some embodiments, at least one 10.16 cm (i.e., four (4) inch) inner diameter stainless metal tube is anchored to an upstream 30.48 cm, (i.e., twelve (12) inch) to 45.72 cm (i.e., eighteen (18) inch) inner diameter pipe that is in mechanical communication with main sampling conveyance line 7. In another alternative embodiment, the tube 11 is a polyvinyl chloride ("PVC") tube containing a plurality of apertures (wastewater diffusers 11a). In another embodiment, the tube 11 is comprised of a rubber medium. In yet another alternative embodiment, the tubing is comprised of a material other than stainless metal, PVC, or rubber. The plurality of apertures 11a may be manufactured on the ventral portion of the tube 11, submerged in the flowing effluent, and facilitate effluent flow diffusion (wastewater diffuser elements 11a).

In another alternative embodiment, the tube 11 is inserted into an upstream rubber cone (not shown per se) which is in mechanical communication with main sampling conveyance line 7. In another alternative embodiment, the tube 11 is coupled to main sampling conveyance line 7 using an at least 12.7 cm (i.e., five (5) inch) diameter support ring (not shown). In another alternative embodiment, the tube 11 is inserted into and covered with a fine microplastic capture filter 12 that is secured to the tube 11 using an at least 10.16 cm (i.e., four (4) inch) diameter rubber tube ring (not shown). The encapsulation of the tubing 11 inside the powder capture net 9 promotes microplastic powder and pellet retention as the effluent continues to flow through the downstream portion of the channel bay 8. In another alternative embodiment, the P3CN 9 includes a distal open end with a built-in diffusor tube 11 to facilitate continuous flow of effluent while also dissipating effluent flow in the event flow pressure becomes too high. The eventual retention of the microplastic pellet and powder residue by the microplastic capture filter 12 facilitates subsequent pellet and powder accumulation for eventual morphological and visual inspection.

As can be seen in FIGS. 1 and 3-4, the channel bay 8 may include a sediment and powder bay 10, which is positioned within the channel bay 8 and downstream and distal to the P3CN 9. The sediment and powder bay 10 provides a reservoir volume in which the wastewater (W) flow diminishes and diffuses before leaving the channel bay 8, thereby allowing smaller sized microplastics (e.g., especially flakes, powders, etc.) which may be present in the wastewater (W), even after passing through the P3CN 9, to settle out of the wastewater (W) and accumulate for visual identification, capture and recovery. In other words, the distal placement of the sediment and powder bay 10 permits dampening and decreasing of the wastewater effluent flow rate and, thereby, facilitates aggregation and conglomeration of remaining microplastics along the distal perimeter of the concrete channel bay 8 for visual and morphological inspection and sampling.

As shown in each of FIGS. 1 and 3-4, the sediment and powder bay 10 may include one or more stoppers or baffles 10*a*, which may be constructed of concrete or other material such as plastic, rubber or metal, and are strategically placed at an upstream portion of the sediment and powder bay 10, for further dampening and slowing the wastewater flow through the channel bay 8 and permitting accumulation of microplastics along the walls of the channel bay 8 for easy identification. Since microplastic powders have physical properties including the tendency to float on the surface of water and aggregate, the one or more baffles 10*a* in the sediment and powder bay 10 allow for microplastics powder to easily congregate on the surface of the water and around the corners of the channel bay 8, thus increasing visibility to the naked eye for easy identification of microplastics by operator personnel monitoring the bays 8, 10 of the solids monitoring and separation mechanism SMSM.

Remaining wastewater effluent (W) in the channel bay 8 then flows past the sediment and powder bay 10 through security gate 13 and into downstream sump 13*b*, from which water pump 14 pulls the wastewater effluent through a return pipe 15 having inner diameter of from about 10.16 cm (i.e., four (4) inches) to about 20.32 cm (i.e., eight (8) inches), and facilitates recycling and re-integrating of the treated wastewater effluent (W) back into main line 1*a* (see direction of arrow R in FIGS. 1 and 3-4). The return pipe 15 is connected to and in fluid communication with the main line 1*a*.

The foregoing description comprises illustrative embodiments of the invention explained and contemplated. Having thus described exemplary embodiments of the present invention, it should be noted by those skilled in the art that the within disclosures are exemplary only, and that various other alternatives, adaptions, variations, and modifications may be made within the scope of the present invention. For instance, listing or numbering the steps of a method or process in a certain order does not constitute any limitation on the order of the steps of that method or process.

Many modifications and other embodiments of the invention will come to mind to one skilled in the art to which this invention pertains having the benefit of the teachings in the foregoing descriptions. Although specific terms may be employed herein, they are used only in a generic and descriptive sense and not for purposes of limitation. Accordingly, the invention described and contemplated herein is not limited to the specific embodiments illustrated hereinabove.

We claim:

1. A solids monitoring and separation mechanism for facilitating visual determination of presence of solids comprising microplastics in water and separating at least a portion of the solids comprising microplastics from the water, the mechanism comprising:

a conveyance pipe which provides diverted flowing water from a source for monitoring and sampling;

a channel bay having an inlet, a sediment and powder bay positioned distally from the inlet, and an outlet positioned downstream of the sediment and powder bay, wherein the channel bay receives and channels the diverted flowing water, from the conveyance pipe, through the inlet, through the sediment and powder bay, and then exit through the outlet;

a capture net which is positioned proximate to and in fluid communication with the inlet of the channel bay to receive the diverted flowing water and capture and separate at least a portion of solids from the diverted flowing water, the capture net including at least one compartment which includes a mesh having aperture size selected to capture and separate a desired size fraction of microplastics from the diverted flowing water; and wherein the sediment and powder bay is further positioned in the channel bay distally from and downstream of the capture net and allows the flowing water to slow, after leaving the capture net and before exiting the channel bay, which facilitates floating and conglomeration of microplastics remaining in the flowing water after flowing through the capture net, thereby increasing visibility of microplastics remaining in the water and further enabling visual detection of microplastics present in the diverted flowing water.

2. The mechanism of claim 1, wherein the water is wastewater produced by a manufacturing facility or wastewater treatment facility, and the solids comprise microplastics.

3. The mechanism of claim 1, further comprising a main line which provides a diverted portion of the flowing water from the source to the conveyance pipe, wherein the conveyance pipe receives the diverted portion of the flowing water and provides it to the inlet of the channel bay.

4. The mechanism of claim 1, wherein the capture net comprises at least an upper compartment and a lower compartment, wherein the upper compartment comprises a first coarse mesh for capturing and separating larger sized solids, and the lower compartment comprises a second finer mesh for capturing and separating smaller sized solids, and wherein the diverted flowing water flows sequentially through the upper compartment first, then through the lower compartment, and into the downstream sediment and powder bay.

5. The mechanism of claim 4, wherein the first coarse mesh includes apertures having size from about 0.79385 mm to about 1.5875 mm, and the second finer mesh includes apertures having size from about 200 microns to about 500 microns.

6. The mechanism of claim 1, wherein the sediment and powder bay comprises one or more baffles for further slowing the flow of the flowing water as it flows therethrough and further facilitating at least a portion of solids present in the flowing water, after flowing through the capture net, to conglomerate and separate from the flowing water, thereby further increasing visibility of conglomerated and separated solids and further enabling visual detection of solids present in the diverted flowing water.

7. The mechanism of claim 1, further comprising a tube positioned within the capture net and having an inlet connected to and in fluid communication with the inlet of the channel bay for receiving diverted flowing water and an outlet allowing the diverted flowing water to exit the tube, wherein the tube includes a diffuser feature through which at least a portion of the diverted flowing water flows before exiting the tube.

8. The mechanism of claim 7, wherein the diffuser feature of the tube comprises a plurality of apertures positioned on a ventral portion of the tube, each of the apertures having a size of from about 127 mm to about 254 mm.

9. The mechanism of claim 8, wherein the tube has a covering attached thereto and comprising a fine solids capture filter having apertures of size from about 200 microns to about 500 microns for capturing and separating smaller solids from the diverted flowing water as it flows through the tube.

10. The mechanism of claim 1, further comprising a main line which provides flowing water from the source to the conveyance pipe and a return pipe, wherein the conveyance pipe receives a diverted portion of the flowing water from the main line and provides it to the inlet of the channel bay of the solids monitoring and separation mechanism, and wherein the solids monitoring and separation mechanism comprises a pump, an upstream end of the return pipe being connected to and in fluid communication with the pump and a downstream end of the return pipe being connected to and in fluid communication with the main line, thereby recycling the diverted flowing water back to the main line.

11. A water monitoring, sampling, and separation system comprising: a water sampling mechanism for determining the presence of solids in water by continuous and passive monitoring and collection of water for analysis, the water sampling mechanism comprising:
an intake pipe which provides diverted flowing water from a source for monitoring and sampling, wherein the intake pipe includes an inlet and an outlet;
an automatic sampler in direct or indirect fluid communication with the intake pipe for collecting one or more samples of the water flowing through the intake pipe, either at predetermined time intervals, or when triggered to do so by receiving a signal, or both; and
a sensor attached on or proximate to the intake pipe at a position upstream of the automatic sampler and which is capable of continuous and passive monitoring of the water for the presence of solids and producing monitoring results comprising at least one solids value, and continuous and passive analyzing of the monitoring results, wherein analyzing comprises comparing the at least one solids value to a predetermined threshold value and, if the solids value is greater than the predetermined threshold value, providing the signal to the automatic sampler to collect one or more samples of the water; and
the solids monitoring and separating mechanism of claim 1,
wherein the water sampling mechanism and the solids monitoring and separating mechanism are arranged in series with one another and wherein the outlet of the intake pipe is connected to and in fluid communication with the inlet of the channel bay, either directly or by the conveyance line.

12. A method for monitoring, detecting and separating solids from water, the method comprising the steps of providing flowing water from a source to the conveyance pipe of the solids monitoring and separation mechanism of claim 1, wherein the water is wastewater produced by a manufacturing facility or wastewater treatment facility and the solids comprise microplastics; and recycling at least a portion of the flowing water back to the source.

13. The mechanism of claim 1, further comprising a downstream sump positioned at the outlet of the channel bay for receiving diverted flowing water exiting from the channel bay.

14. The mechanism of claim 13, further comprising a pump to facilitate providing and recycling the diverted flowing water from the outlet of the channel bay or the sump to the source.

\* \* \* \* \*